United States Patent [19]

Castleman et al.

[11] 4,238,678
[45] Dec. 9, 1980

[54] APPARATUS AND A METHOD FOR DETECTING AND MEASURING TRACE GASES IN AIR OR OTHER GASEOUS BACKGROUNDS

[75] Inventors: B. Wayne Castleman, Kenneth City; Gene B. Wyatt, Seminole, both of Fla.

[73] Assignee: Honeywell Inc., Minneapolis, Minn.

[21] Appl. No.: 948,740

[22] Filed: Oct. 5, 1978

[51] Int. Cl.$^2$ .................... H01J 39/28; G01T 1/185; B01D 59/44
[52] U.S. Cl. ................................ 250/381; 250/287; 250/382; 250/384; 250/385
[58] Field of Search .............. 250/282, 287, 384, 382, 250/283, 286, 288, 379, 381, 385

[56] References Cited
U.S. PATENT DOCUMENTS

| | | | |
|---|---|---|---|
| 3,626,181 | 12/1971 | Wernlund | 250/287 |
| 3,629,574 | 12/1971 | Carroll | 250/282 |
| 4,119,851 | 10/1978 | Castleman et al. | 250/382 |

*Primary Examiner*—Alfred E. Smith
*Assistant Examiner*—Carolyn E. Fields
*Attorney, Agent, or Firm*—Albin Medved

[57] ABSTRACT

Method and apparatus for detecting the presence of very small concentrations of certain vapors and gases in air or other gaseous backgrounds. A gas sample is ionized by a source of ionizing radiation. The ionized gas is then directed through a first drift region where the ions are subjected to a drift potential. Electrical biased grid means are provided to allow only heavier ions of lower mobility to pass through the first drift region into a second drift region, where electrical shutter means are provided to allow discrete packets of ions to pass and to drift at speeds depending upon their mobilities and be detected. In an alternate embodiment, the first draft region is positioned downstream from the second drift region.

4 Claims, 1 Drawing Figure

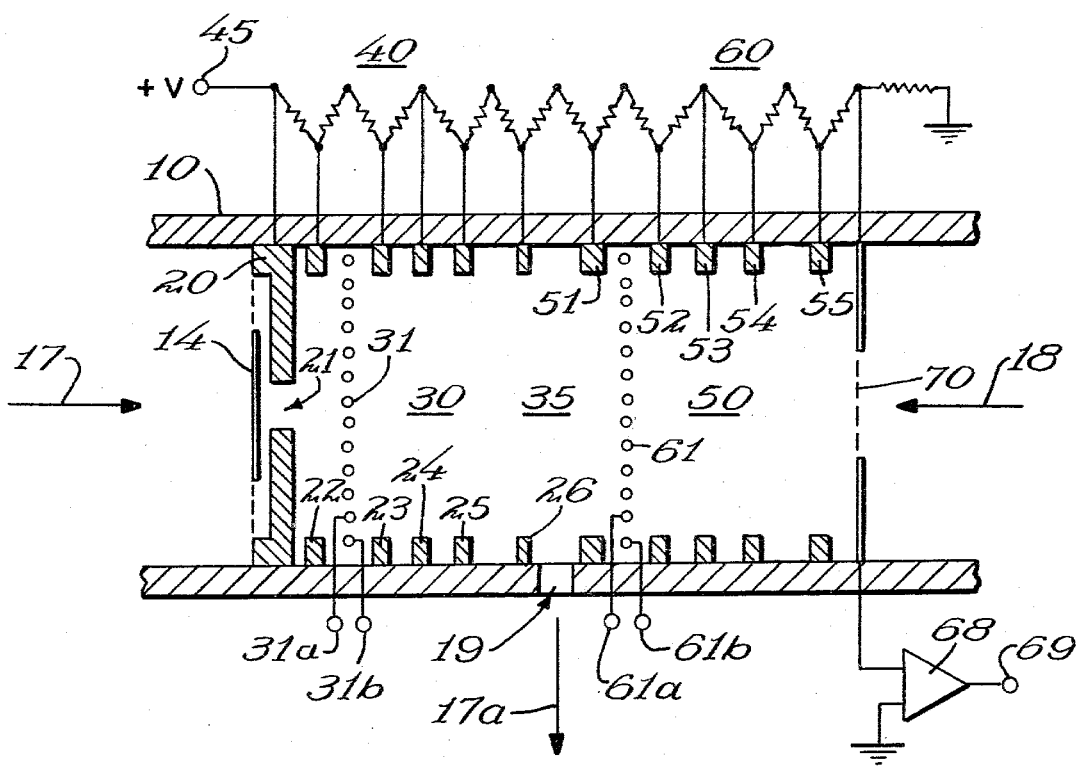

APPARATUS AND A METHOD FOR DETECTING AND MEASURING TRACE GASES IN AIR OR OTHER GASEOUS BACKGROUNDS

BACKGROUND OF THE INVENTION

The invention relates to apparatus for detection of small amounts of vapors or gases in an atmosphere of air or other gas. It combines the features of a first drift tube having electric conductive grids with constant potentials and a second drift tube having conductive grids with modulated potentials. By thus combining the two drift tubes, advantages of both are attained resulting in performance which is superior to that of either one of them individually.

Prior art apparatus for detection of trace gases includes ionization cells such as described in U.S. Pat. No. 3,835,328. In the ionization cell, trace gases are detected by directing a sample of gas past a source of ionizing radiation and then through a recombination region to an ion collector.

An alternative means for detection of trace gases or vapors is a drift tube. In a drift tube, vapors or gases are subjected to ionizing radiation in the same manner as in the ionization cell. In a drift tube, however, the resulting ions are placed in an electric field, causing the ions to migrate in a predetermined direction, where different types of ions can be separated, detected, and measured by virtue of the difference of velocity or mobility of the ions in an electric field. Ion shutter grids or gates are provided for segregating the ions in accordance with their drift time.

U.S. Pat. No. 4,119,851 teaches an apparatus which achieves improvement in selectivity of vapors or gases by combining the features of an ionization cell and a drift tube. The apparatus can take form in two basic configurations. In one configuration, the ionization cell operates as a pre-selector or pre-filter which eliminates or reduces the effects of the great majority of possible interfering ion species while allowing a significant fraction of the ions of interest to pass through. The drift tube then receives the selected ions and further classifies the ions on the basis of their mobility. In an alternate configuration, the drift tube is positioned upstream of the ionization cell.

SUMMARY OF THE INVENTION

In accordance with the present invention, the sensitivity and selectivity in detection of trace gases and vapors is enhanced by combining the features of two types of drift tubes. In a first drift tube, the electric grids are energized with constant potentials. The grids in the drift tube operate as an electrical analog to the baffles in an ionization cell that provide a means for capturing lighter, higher mobility ions, while allowing a greater number of heavier, lower mobility ions to pass. An advantage of using a drift tube in place of an ionization cell is that a much greater number of ions survive the passage through the constant potential grids than through the recombination region of an ionization cell. Sensitivity and stability are thereby improved. The other drift tube contains electric grids to which modulated potentials are applied. Through the application of the modulated potentials, the grids act as electric shutters, allowing discrete packets of ions of a specified mobility to pass through, while blocking the passage of other ions.

The gas sample under test is drawn past a radioactive source and a fraction of it becomes ionized. The ions thus created move under the influence of a constant potential into the first drift tube. In the first drift tube, a grid is maintained at a constant potential. The alternate conductors of the grid are maintained at different constant potentials such that the ions of higher mobility are preferentially collected while those of lower mobility are allowed to pass through. The ions that pass through the first drift tube then enter the second drift tube and arrive at a coplanar electrical shutter which allows a discrete packet of ions to enter the drift tube. The various types of ions drift at speeds characteristic of their mobility. Each specie of ions with its characteristic mobility will arrive at a collector in the drift tube at a specific time.

The first drift tube acts as a prefilter for the second drift tube, resulting in a performance which is superior to that achieved by either one standing alone. In an alternate embodiment of the present invention, the two drift tubes are reversed in position, the tube with constant grid potentials being placed downstream from the tube with modulated grid potentials.

BRIEF DESCRIPTION OF THE DRAWING

The single FIGURE of the drawing illustrates a preferred embodiment of the present invention.

DESCRIPTION OF THE PREFERRED EMBODIMENT

Referring to the FIGURE of the drawing, a preferred embodiment of the present invention is shown having a housing 10 constructed of non-conductive material, such as Teflon. Mounted within housing 10, at a first end, is a radiation emitting source 14, which consists of a metal screen to which is affixed a radiation emitting foil. The gas sample to be detected is received from the direction shown by arrow 17. A conductive plate 20, having a central opening 21, separates radiation source 14 from a drift region 30. The other end of drift region 30 (the downstream end) is defined by a region 35 wherein the sample gas stream combines with the flow of clean air or gas from the direction indicated by arrow 18.

A plurality of conductive rings 22, 23, 24, 25, and 26 are mounted within drift region 30 and are connected to an electric potential source 45 via a voltage divider network 40. Electric potential source 45, in conjunction with voltage divider network 40, establishes a linear electric field between plate 20 at the upstream end and conductive ring 26 at the downstream end of drift region 30. An electrically conductive grid 31 is positioned in a plane normal to the gas flow between guard rings 22 and 23 near the upstream end of drift region 30. Grid 31 is comprised of a plurality of electric conductors, the alternate of which are connected to each other such that a different voltage can be applied to alternate conductors in each grid at terminals 31a and 31b, respectively.

A second drift region identified with numeral 50 is located downstream from drift region 30. In drift region 50, electrically conductive guard rings 51, 52, 53 54 and 55 are mounted about the periphery of the drift region in the manner shown. A collector electrode 70 is mounted in a plane perpendicular to the direction of gas flow at the downstream end of drift region 50. A voltage divider network 60 connects guard rings 51 through 55 and collector electrode 70 to electric potential source 45 via voltage divider network 40. Electric potential source 45, together with divider network 40, establishes a linear electric field in drift region 50 between guard ring 51 and collector 70.

A counter flow of clean air flows continuously in the direction shown by arrow 18 and serves to prevent ion-molecule reactions from occurring in drift region 50. The two streams of gas combine in region 35 and the resulting gas mixture is pumped out through port 19 in the direction shown by arrow 17a. In an alternate and equally effective mode of operation, the gas sample can be introduced through port 19 in a direction opposite arrow 17a and the two gas streams (17a reversed and 18) will combine and be pumped out from the left side of housing 10 in a direction opposite arrow 17.

A grid 61 is positioned in drift region 50 between guard rings 51 and 52 in a plane normal to the direction of gas flow. As in the case of grid 31 in drift region 30, grid 61 has alternate conductors electrically connected to each other such that the alternate conductors can be energized with different voltage at terminals 61a and 61b, respectively.

Collector electrode 70 is connected to the input of an amplifier 68, which has an output 69.

In the preferred embodiment of the invention shown in the drawing, the gas sample is received from the direction of arrow 17 and is directed past radioactive source 14 into drift region 30. The gas sample becomes ionized at the radioactive source 14 by charge transfer process. The resulting ions move under the influence of a constant potential established in region 30. A further much lesser influence on the motion of the ions is the constant flow of the gas through the tube. Grid 31 is operated as a co-planar electrical shutter. By applying appropriate constant potentials to terminals 31a and 31b of grid 31, the shutter is biased partially open to allow only ions of lower mobility to enter into drift region 30. Grid 31, with the difference potentials between the alternate conductors, acts very much like the recombination region of an ionization cell. That is, the grid operates as an electrical analog to baffles, providing a means for capturing the lighter, higher mobility ions, while allowing a greater number of heavier, lower mobility ions to pass through to the second drift tube. A major advantage of using grid 31 in the manner described, as opposed to passing ions through a recombination region, is that the present approach allows a much greater concentration of ions to survive and reach grid 61. The sensitivity and stabiltiy of the cell are thereby improved.

The ions emerging from drift region 30 enter drift region 50. As stated previously, a linear electric field is established in drift region 50 by electric potential source 45 through divider networks 40 and 60, connected to guard rings 51 through 55 and collector 70. The alternate conductors in grid 61 are energized such that a different potential can briefly exist between adjacent conductors, while the average potential of each grid is equal to the linear drift potential at the location of the respective grid. The ions emerging from drift region 30 and passing through region 35 (wherein the gas streams combine) reach grid 61 in a steady stream. By applying appropriate potentials to terminals 61a and 61b of grid 61, the shutter opens briefly to allow a discrete packet of ions to enter drift region 50. Each ion species drifts at a speed which is characteristic of its mobility. Therefore, when several ion species are present they can be separately detected by their different arrival times at collector 70.

Collector 70 is connected to the input of an amplifier 68, whose output 69 will provide the signal indicating the presence of particular ions in the gas sample. The amplitude of the signal is a function of the number of ions detected.

In the operation of the preferred embodiment described above, grid 31 in recombination region 30 was energized with constant potentials, while grid 61 of recombination region 50 was energized with modulated potentials. The invention operates satisfactorily with the functions of the two drift cells reversed, i.e. by energizing grid 31 with modulated potentials and using constant potentials at grid 61.

While in the preferred embodiment of the present invention drift regions 30 and 50 are shown to be of about the same size, the invention works equally well with drift regions of different sizes, both in length and diameter. The placement of grid 31 and the constant potentials applied thereto can be selected to obtain a particular desired effect on the ion species produced and transmitted through region 30.

A unique and improved apparatus for sensing and measuring gaseous impurities has been shown and described in the foregoing specification. Various modifications of the inventive concepts will be obvious to those skilled in the art, without departing from the spirit of the invention. It is intended that the scope of the invention be limited only by the following claims.

What is claimed is:

1. An apparatus for detecting trace amounts of vapors or gases in air or other gaseous backgrounds, said apparatus comprising:
   a housing defining a passage for flow of gas through first and second drift regions;
   a source of ionizing radiation positioned in said passage near said first drift region for creating ions in said gas;
   a collector electrode mounted within said housing near said second drift region;
   means for establishing a substantially linear drift potential in said housing for causing said ions to drift from said source of ionizing radiation toward said collector electrode through said first and second drift regions;
   an electrically conductive grid means located in said first drift region, said grid being comprised of a plurality of conductors biased at predetermined constant electric potentials for selectively collecting ions of higher mobility, while allowing lower mobility ions to pass through to said second drift region;
   gating means located in said second drift region for allowing selected groups of ions from said first drift region to pass through into said second drift region and onto said collector electrode at times proportional to their mobility; and
   means for measuring the number of ions reaching said collector electrode.

2. Apparatus according to claim 1, wherein said gating means is comprised of a plurality of conductors, alternate of said conductors being connected to first and second terminals, whereby said gating means can be operated by application of appropriate potentials to said terminals to allow discrete packets of ions to enter into said second drift region.

3. Apparatus according to claim 1, wherein said gating means is located in said first drift region and said electrically conductive grid means is located in said second drift region.

4. Apparatus according to claim 3, wherein said gating means is comprised of a plurality of conductors, alternate of said conductors being connected to first and second terminals, whereby said gating means can be operated by application of appropriate potentials to said terminals to allow discrete packets of ions to enter into said first drift region.

* * * * *